(12) United States Patent
Nagura

(10) Patent No.: US 8,293,261 B2
(45) Date of Patent: Oct. 23, 2012

(54) INTRAVASCULAR IMPLANT

(75) Inventor: Hiroaki Nagura, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 528 days.

(21) Appl. No.: 11/883,056

(22) PCT Filed: Jan. 26, 2006

(86) PCT No.: PCT/JP2006/301196
§ 371 (c)(1),
(2), (4) Date: Jul. 26, 2007

(87) PCT Pub. No.: WO2006/080381
PCT Pub. Date: Aug. 3, 2006

(65) Prior Publication Data
US 2008/0262589 A1    Oct. 23, 2008

(30) Foreign Application Priority Data
Jan. 28, 2005   (JP) ................. 2005-021163

(51) Int. Cl.
*A61F 2/82* (2006.01)
*A61F 2/06* (2006.01)
*A61F 2/00* (2006.01)

(52) U.S. Cl. ....... 424/423; 623/1.2; 623/1.42; 623/1.43; 623/1.1

(58) Field of Classification Search .............. 424/423
See application file for complete search history.

(56) References Cited

U.S. PATENT DOCUMENTS

| | | | |
|---|---|---|---|
| 5,298,218 A | | 3/1994 | Groll et al. |
| 5,728,079 A | | 3/1998 | Weber et al. |
| 2001/0007955 A1 | * | 7/2001 | Drasler et al. ............ 623/1.15 |
| 2002/0004060 A1 | * | 1/2002 | Heublein et al. ........... 424/422 |
| 2003/0153972 A1 | * | 8/2003 | Helmus .................... 623/1.15 |
| 2004/0045639 A1 | | 3/2004 | Kikawa et al. |
| 2004/0073297 A1 | | 4/2004 | Rohde et al. |
| 2004/0098108 A1 | | 5/2004 | Harder et al. |
| 2004/0158309 A1 | | 8/2004 | Wachter et al. |
| 2004/0241036 A1 | | 12/2004 | Meyer-Lindenberg et al. |
| 2006/0177379 A1 | * | 8/2006 | Asgari ......................... 424/9.3 |
| 2006/0259126 A1 | * | 11/2006 | Lenz ........................ 623/1.16 |

FOREIGN PATENT DOCUMENTS

| | | |
|---|---|---|
| JP | 5-194133 A | 8/1993 |
| JP | 8-173543 A | 7/1996 |
| JP | 2001-511049 A | 8/2001 |
| JP | 2004-73859 A | 3/2004 |
| JP | 2004-160236 A | 6/2004 |
| JP | 2004-244726 A | 9/2004 |
| WO | WO 02/100452 A1 | 12/2002 |

OTHER PUBLICATIONS

Lambertus et al. Improved Visualization in Metallic Stents and Filters by Reduction of Susceptibility and RF Artifacts. 2001. http://cds.ismrm.org/ismrm-2001/PDF2/0305.pdf.*
Nie et al. Enhanced Age Hardening Response and Creep Resistance of Mg-Gd Alloys Containing Zn. Scripta Materialia 53 (Jul. 2005) pp. 1049-1053.*
http://en.wikipedia.org/wiki/Stent (Wikipedia article on stents), Retrieved from online on Sep. 25, 2009.*
International Search Report for PCT/JP2006/301196 dated Apr. 4, 2006.
Köster, Ralf et al., "Nickel and molybdenum contact allergies in patients with coronary in-stent restenosis", The Lancet, England, Elsevier Limited, Dec. 2, 2000, vol. 356, No. 9245, pp. 1895-1897.
International Preliminary Report on Patentability PCT/IB/373 (including PCT/ISA/237) dated Aug. 9, 2007 for International Application No. PCT/JP2006/301196.
Database Inspec (Online) The Institution of Electrical Engineers, Stevenagem GB, 2004. Lyon P: "New Magnesium Alloy for Aerospace and Specialty Applications" XP-002664257 Mar. 2004.
Extended European Search Report issued on Dec. 2, 2011 in the corresponding European Patent Application No. 06712378.6-1219/1842507 PCT/JP2006301196.

* cited by examiner

*Primary Examiner* — David J Blanchard
*Assistant Examiner* — Sarah Alawadi
(74) *Attorney, Agent, or Firm* — Buchanan Ingersoll & Rooney PC

(57) ABSTRACT

The invention has for its object the provision of an intravascular implant that has mechanical characteristics and physiological characteristics and is very low in cell cytotoxicity and provides an intravascular implant having an implant body made of a metal material that contains gadolinium and magnesium and is free of yttrium.

19 Claims, 2 Drawing Sheets

INTRAVASCULAR IMPLANT

TECHNICAL FIELD

This invention relates to an intravascular implant used inside a living body of a person or animal.

BACKGROUND ART

Various types of intravascular implants are known including a stent, balloon, cannula, coil, pin and the like. These are employed for treatment of the blood vessel of a person or animal.

Such intravascular implants are required to have various functions and characteristic properties.

For instance, with a stent, such characteristics as mechanical characteristics (high strength, high hardness, high ductility, low recoiling property and the like) and physiological characteristics (prevention of stenosis and restenosis, biodegradability, metal allergy prevention and the like) are required.

For the purpose of meeting these requirements, many studies have been conventionally made with respect to the composition of a material for intravascular implant.

For instance, in Patent Document 1, in order to provide a mechanically and physiologically improved internal artificial organ (stent or the like), there is a description concerning an internal artificial organ of a type having a support structure containing a metal material. The internal artificial organ is characterized in that the metal material includes a magnesium alloy of the following composition: magnesium=>90%, yttrium=3.7% to 5.5%, rare element=1.5% to 4.4%, and residues=<1%.

For the rare earth element, neodymium alone is exemplified.

For the residues, only two elements of zirconium and lithium are exemplified.

In Patent Document 2, for the purpose of providing medical implants (a stent, clip and the like) made of a biodegradable material having mechanical characteristics, there is a description concerning a medical implant, characterized in that the material includes 79 to 97% of magnesium, 2 to 5% of aluminium, 0 to 12% of lithium and 1 to 4% of rare earth elements.

The medical implant can be degraded by corrosion in the living body.

The rare earth elements exemplified include only four elements of cerium, lanthanum, neodymium and praseodymium.

In Patent Document 3, although the invention has its object for providing a medical implant that does not generate a large quantity of gas and is free of heterogeneous decomposition, it is stated that an alloy made of magnesium-gadolinium-yttrium-zinc is a metal material whose corrosion resistance is good.

In Non-patent Document 1, there is described possible induction of restenosis through metal allergies in case where an implant made of a nickel and molybdenum-containing metal material is placed in the living body.

Patent Document 1: Japanese Patent Laid-open No. 2004-160236
Patent Document 2: Japanese Patent Laid-open No. 2001-511049
Patent Document 3: US2004/0241036 A1
Non-patent Document 1: Koster R et. al, "Nickel and molybdenum contact allergies in patients with coronary in-stent restenosis", The Lancet, England, Elsevier Limited, Dec. 2, 2000, Vol. 356, No. 9245, pp. 1895-1897

DISCLOSURE OF INVENTION

Problem to be Solved by the Invention

As stated hereinabove, many studies have been hitherto made with respect to the compositions of materials for intravascular implants in order to impart mechanical characteristics and physiological characteristics thereto. No study has been ever made with respect to intravascular implants whose cell cytotoxicity is very low in addition to such characteristics.

The cell cytotoxicity is a nature of giving some lesions (death of cell, and some abnormals, lowerings and the like of various functions in which cells take part, such as, proliferating ability, metabolic capability and the like), and should desirably be as low as possible in intravascular implants.

Accordingly, the problem to be solved by the invention is to provide an intravascular implant which has mechanical characteristics and physiological characteristics and are very low in cell cytotoxicity.

Means for Solving the Problem

We have made studies with respect to a diversity of materials and found that an intravascular implant having an implant body made of a metal material containing specific types of metals is able to solve the above problem.

More particularly, the inventions are recited in (1) to (16) below.

(1) An intravascular implant including an implant body made of a metal material which contains gadolinium and magnesium and is free of yttrium.

(2) The intravascular implant as recited in (1) above, wherein the metal material further includes neodymium.

(3) The intravascular implant as recited in (1) or (2) above, wherein a content of the gadolinium ranges 1.0 to 5.0 mass %.

(4) The intravascular implant as recited in (2) or (3) above, wherein a content of the neodymium ranges 1.0 to 5.0 mass %.

(5) The intravascular implant as recited in any one of (1) to (4) above, wherein the metal material further includes zinc.

(6) The intravascular implant as recited in any one of (1) to (5) above, wherein the metal material further includes zirconium.

(7) The intravascular implant as recited in any one of (1) to (6) above, wherein the implant body has, on the surface thereof, a layer made of a composition including a biologically bioactive substance and a biodegradable polymer.

(8) The intravascular implant as recited in any one of (1) to (6) above, wherein the implant body has, on the surface thereof, a layer made of a biologically bioactive substance and a layer made of a biodegradable polymer.

(9) The intravascular implant as recited in (7) or (8) above, wherein the biodegradable polymer contains a plasticizer.

(10) The intravascular implant as recited in any one of (7) to (9), wherein the biologically bioactive substance is at least one member selected from the group consisting of an anticancer drug, an immunosuppressant, an antibiotic, an antirheumatic drug, an antithromobotic drug, an HMG-CoA reductase inhibitor, an ACE inhibitor, a calcium antagonist, an antihyperlipemidic drug, an integrin inhibitor, an antiallergic agent, an antioxidant, a GPIIbIIIa antagonist, a retinoid, a flavonoid, a carotenoid, a lipid improver, a DNA synthesis inhibitor, a tyrosine kinase inhibitor, an antiplatelet drug, an anti-inflammatory drug, a bio-derived material, an interferon and an NO production promoter.

(11) The intravascular implant as recited in any one of (7) to (10) above, wherein the biodegradable polymer is at least one member selected from the group consisting of polyglycollic acid, polylactic acid, polycaprolactone, polyhydroxybutyric acid, cellulose, polyhydroxybutylate valeric acid and a polyorthoester, or a copolymer, mixture or composite material thereof.

(12) The intravascular implant as recited in any one of (9) to (11), wherein the plasticizer is at least one member selected from the group consisting of polyethylene glycol, poyoxyethylenepolyoxypropylene glycol, polyoxyethylenesorbitan monooleate, a monoglyceride and an acetylated monoglyceride, or a mixture thereof.

(13) The intravascular implant as recited in any one of (1) to (12), wherein the implant body is one obtained by laser processing of the metal material having a tubular form.

(14) The intravascular implant as recited in any one of (1) to (12) above, wherein the implant is a stent.

(15) The intravascular implant as recited in (14) above, wherein the stent is a self-expandable stent or a balloon-expandable stent.

(16) The intravascular implant as recited in (14) or (15) above, wherein the stent is a coronary vascular stent or a peripheral stent.

Effects of Invention

The intravascular implant of the invention has required strength, hardness and ductility and is good at processability. The implant is biodegradable and causes a living body to suffer no metal allergies. The implant is very low in cell cytotoxicity in addition to such mechanical characteristics and physiological characteristics.

BEST MODE FOR CARRYING OUT THE INVENTION

Figure 1:
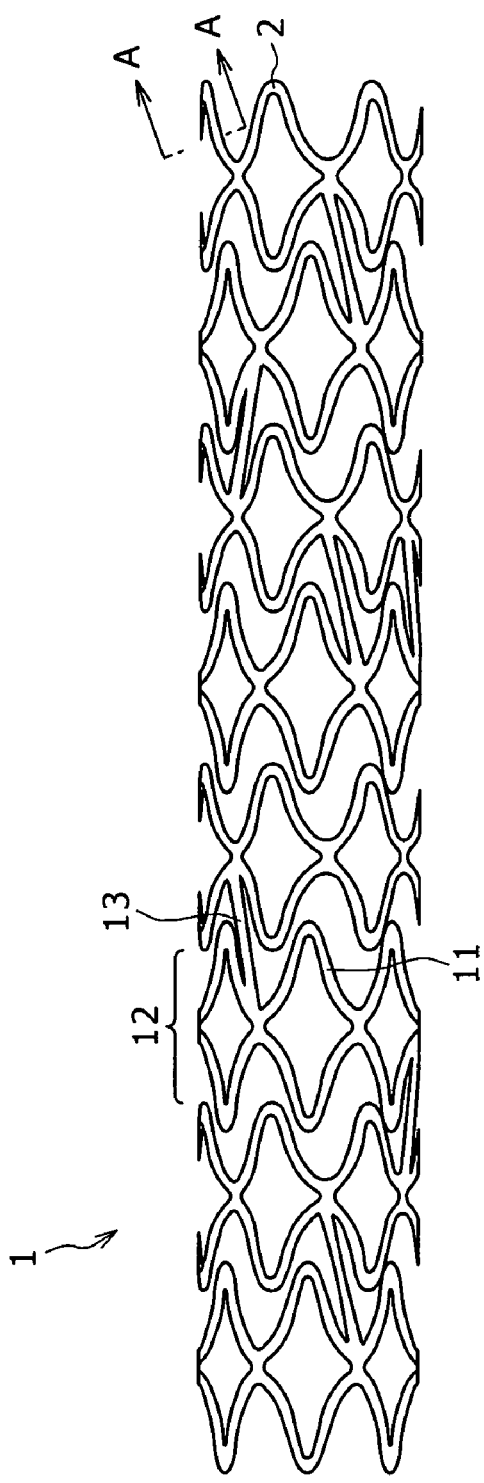
FIG. 1 is a side view showing an embodiment of a stent which is an intravascular implant of the invention.

The invention is directed to an intravascular implant, which includes an implant body made of a metal material which contains gadolinium and magnesium and is free of yttrium.

The metal material that contains gadolinium and magnesium and is free of yttrium may be sometimes referred to hereinafter as "metal material of the invention".

For one instance, mention is made of a metal material composed of magnesium, gadolinium, neodymium, zinc, zirconium and calcium.

In addition, an implant body made of the metal material of the invention may be sometimes referred to hereinafter as "implant body of the invention".

Likewise, an intravascular implant having the implant body of the invention may be sometimes referred to hereinafter as "intravascular implant of the invention".

The metal material of the invention is mainly made of magnesium. More particularly, the content (mass %) of magnesium relative to the total weight of the metal material of the invention is higher than a content (mass %) of gadolinium.

Preferably, the metal material of the invention should further contain neodymium. The reason for this is that while keeping cell cytotoxicity at a low level, strength, hardness, ductility and processability can be further improved.

The content of gadolinium relative to the total weight of the metal material of the invention is preferably at 1.0 to 5.0 mass %, more preferably at 1.0 to 3.0 mass % and most preferably at 1.0 to 1.5 mass %. Within this range, there is obtained such an effect that while keeping the cell cytotoxicity at a low level, strength, hardness, ductility and processability can be more improved.

The content of gadolinium is a value when quantitatively determined according to an ICP emission spectrophotometry using the metal material of the invention as a sample.

The contents, described hereinafter, of neodymium, zinc, zirconium, calcium and magnesium relative to the total weight of the metal material of the invention are, respectively, those values quantitatively determined in a similar manner.

The content of neodymium relative to the total weight of the metal material of the invention is preferably at 1.0 to 5.0 mass %, more preferably at 2.0 to 4.0 mass % and most preferably at 2.0 to 3.1 mass %. Within such a range, while keeping cell cytotoxicity at low level, there is obtained an effect that strength, hardness, ductility and processability can be more improved.

The metal material of the invention should preferably further contain zinc. The reason for this is that the degradation of the implant body of the invention can be prolonged.

The content of zinc relative to the total weight of the metal material of the invention is preferably at 0.1 to 3.0 mass %, more preferably at 0.1 to 1.0 mass % and most preferably at 0.2 to 0.5 mass %. Such a range is preferred from the standpoint that zinc can be uniformly dispersed in the matrix of magnesium and gadolinium.

The metal material of the invention should preferably further contain zirconium. The reason for this is that crystal grains can be made fine with improved ductility.

The content of zirconium relative to the total weight of the metal material of the invention is preferably at 0.1 to 3.0 mass %, more preferably at 0.3 to 1.5 mass % and most preferably at 0.5 to 0.7 mass %. Such a range is preferred from the standpoint that zirconium can be uniformly dispersed in the matrix of magnesium and gadolinium.

The metal material of the invention should preferably further contain calcium. The reason for this is that the degradation of the implant body of the invention can be prolonged.

The content of calcium relative to the total weight of the metal material of the invention is preferably at 0.1 to 3.0 mass %, more preferably at 0.1 to 1.0 mass % and most preferably at 0.1 to 0.5 mass %. Such a range is preferred from the standpoint that calcium can be uniformly dispersed in the matrix of magnesium and gadolinium.

The metal material of the invention should preferably contain magnesium at 80 mass % to 99 mass % relative to the total weight thereof, more preferably at 90 mass % to 99 mass % and most preferably at 94 mass % to 97 mass %. With respect to the components other than magnesium, gadolinium should be essentially contained, along with at least one selected from the group consisting of neodymium, zinc, zirconium and calcium.

The content of magnesium relative to the total weight of the metal material of the invention within such a range as indicated above is preferred. This is because there are achieved such effects as of suppressing the formation of blood clot and making its disappearance in the living body easy upon use of the intravascular implant of the invention. Further, it is also preferable that autogenous ignition and explosion in the manufacturing process are suppressed.

Furthermore, it is more preferred that components other than magnesium of the metal material of the invention essentially contain gadolinium, along with at least one selected from the group consisting of neodymium, zinc, zirconium and calcium and that other components described hereinafter are not substantially contained. The reason for this is that there can be relatively readily obtained an implant body of the invention that can be easily processed, has well-balanced strength and ductility and is very low in cell cytotoxicity. The term "not substantially contained" means that a content relative to the total weight of the metal material of the invention is not larger than 1 mass %.

The metal material of the invention may further include, aside from magnesium and gadolinium and such neodymium, zinc, zirconium and calcium as mentioned above, components which do not adversely influence the human body and animals to which the intravascular implant of the invention is applied. For such components, mention is made, for example, of carbon, hydroxyapatite, polylactic acid, polyethylene glycol, and mixtures of arbitrary combinations thereof. These components are all low in cell cytotoxicity. The content ratios of these components may be within ranges not lowering the mechanical characteristics and physiological characteristics of the implant body of the invention. For instance, the contents are preferably at not larger than 1 mass % relative to the total weight of the metal material of the invention, more preferably at not larger than 0.7 mass %.

Preferably, the metal material of the invention should contain magnesium and gadolinium, neodymium, zinc, zirconium and calcium, and the components not adversely influencing the human body and animals described above, and should not substantially contain components other than those indicated above. This is because of ease in processability, well-balanced strength and ductility, and very low cell cytotoxicity. Again, the term "not substantially contain" means a content of not larger than 1 mass % relative to the total weight of the metal material of the invention.

Especially, it is preferred that the metal material of the invention should not contain yttrium, and should not also contain chromium, nickel, vanadium, silver, mercury, gallium, copper, cobalt and lead if circumstances allow.

The term "not contain yttrium" indicates that a content of yttrium in the metal material is at not larger than 0.1 mass %.

As will be described hereinafter, the present inventors made clear that these components are high in cell cytotoxicity. Accordingly, it is preferred that starting materials (materials) used for the manufacture of the implant body of the invention should be selected from ones that do not contain these components when possible. In the manufacturing step of the implant of the invention, it is preferred not to permit these components to be incorporated therein.

The intravascular implant of the invention should preferably have, on the surface of the implant body of the invention made of such a metal material as set out hereinabove, a layer made of a composition which includes a biologically bioactive substance and a biodegradable polymer. This is because as the biodegradable polymer decomposes, the biologically bioactive substance is slowly released into the blood vessel, ensuring appropriate treatment.

The compositional ratio (ratio by weight) between the biologically bioactive substance and the biodegradable polymer in the composition including the biologically bioactive substance and the biodegradable polymer is at 1:99 to 99:1, preferably at 30:70 to 70:30. This is because while taking the physical properties and degradability of the biodegradable polymer into account, the biologically bioactive substance is to be loaded in amounts as much as possible.

Using the composition, the layer is formed on the surface of the implant body of the invention according to a method described hereinbelow.

The layer thickness is set at 0.1 to 100 μm, preferably at 1 to 30 μm and more preferably at 5 to 15 μm. The layer whose thickness is within such a range as indicated above is advantageous in that it can be easily inserted into the blood vessel and the biologically bioactive substance can be loaded in the surface of the implant in amounts necessary for the treatment of a lesioned part.

Preferably, the intravascular implant of the invention has, on the surface of the implant body of the invention, separate layers that are, respectively, formed of a biologically bioactive substance and a biodegradable polymer. In doing so, there are achieved effects of stabilizing the biologically bioactive substance and enabling the biologically bioactive substance to be released in the blood vessel in a stepwise manner.

Especially, when the layer made of a biodegradable polymer is formed on the surface of the implant body of the invention and the layer made of a biologically bioactive substance is further formed thereon, the implant body of the invention is not in direct contact with the biologically bioactive substance, so that no unnecessary chemical reaction or the like takes place therebetween, thereby preventing the biologically bioactive substance from degradation or deterioration.

The layer made of a biologically bioactive substance and the layer of a biodegradable polymer are, respectively, formed on the surface of the implant body according to the procedure described hereinafter.

The thickness of the layer of a biologically bioactive substance is at 0.1 to 100 μm, preferably at 1 to 15 μm and more preferably at 3 to 7 μm. The thickness of the layer made of a biodegradable polymer is at 0.1 to 100 μm, preferably at 1 to 15 μm and more preferably at 3 to 7 μm. The layers whose thicknesses are within such ranges are advantageous in that easy insertion into the blood vessel is allowed and while taking the physical properties and degradability of the biodegradable polymer into account, the biologically bioactive substance can be loaded on the implant surface in an amount necessary for treatment of a lesioned part.

It will be noted that with the intravascular implant of the invention, the layer of a biologically bioactive substance and the layer of a biodegradable polymer, formed on the surface of the implant body of the invention, may be plural in number, respectively.

The biodegradable polymer preferably contains a plasticizer, for which there is achieved an effect of preventing the layer containing the biodegradable polymer from cracking or dropping off as would be otherwise caused in the course of deformation of the intravascular implant.

The biologically bioactive substance is not critical in type so far as it is able to inhibit the stenosis and blockage of the blood vessel as will occur when the intravascular implant of the invention is placed at a lesioned part and can be arbitrarily selected. For instance, it is preferred from the standpoint that a lesioned part can be treated by controlling the behavior of cells of the tissue at a lesioned part to use at least one selected from the group consisting of an anticancer drug, an immunosuppressant, an antibiotic, an antirheumatic drug, an antithromobotic drug, an HMG-CoA reductase inhibitor, an ACE inhibitor, a calcium antagonist, an antihyperlipemidic drug, an integrin inhibitor, an antiallergic agent, an antioxidant, a GPIIbIIIa antagonist, a retinoid, a flavonoid, a carotenoid, a lipid improver, a DNA synthesis inhibitor, a tyrosine kinase inhibitor, an antiplatelet drug, an anti-inflammatory drug, a bio-derived material, an interferon and an NO production promoter.

The anticancer drug preferably includes, for example, vincristine, vinblastine, vindesine, irinotecan, pirarubicin, paclitaxel, docetaxel, methotrexate and the like.

The immunosuppressant preferably includes, for example, sirolimus, tacrolimus, azathioprine, cyclosporine, cyclophosphamide, mycophenolate mofetil, everolimus, ABT-578, AP23573, CCI-779, gusperimus, mizoribine and the like.

The antibiotic includes, for example, mitomycin, adriamycin, doxorubicin, actinomycin, daunorubicin, idarubicin, pirarubicin, aclarubicin, epirubicin, peplomycin, zinostatin stimalamer, and the like.

The antirheumatic drug preferably includes, for example, methotrexate, sodium thiomalate, penicillamine, lobenzarit and the like.

The antithromobotic drug preferably include, for example, heparin, aspirin, antithrombin, ticlopidine, hirudin and the like.

The HMG-CoA reductase inhibitor preferably includes, for example, cerivastatin, cerivatatin sodium, atorvastatin, rosuvastatin, pitavastatin, fulvastatin, fulvastatin sodium, simvastatin, lovastatin, pravastin and the like.

The ACE inhibitor preferably includes, for example, quinapril, perindopril erbumine, trandolapril, cilazapril, temocapril, delapril, enalapril maleate, lisinopril, captopril and the like.

The calcium antagonist preferably includes, for example, fifedipine, nilvadipine, diltiazem, benidipine, nisoldipine and the like.

The antihyperlipemidic drug preferably includes, for example, probucol.

The integrin inhibitor preferably includes, for example, AJM300.

The antiallergic agent preferably includes, for example, tranilast.

The antioxidant preferably includes, for example, α-tocopherol.

The GPIIbIIIa antagonist preferably includes, for example, abciximab.

The retinoid preferably includes, for example, all-trans retinoic acid.

The flavonoid preferably includes, for example, epigallocatechin, anthocyanin and proanthocyaninidin.

The carotenoid preferably includes, for example, β-carotene and lycopene.

The lipid improver preferably includes, for example, eicosapentanoic acid.

The DNA synthesis inhibitor preferably includes, for example, 5-FU.

The tyrosine kinase inhibitor preferably includes, for example, genistein, tyrphostin, erbstatin, staurosporine and the like.

The antiplatelet drug preferably includes, for example, ticlopidine, cilostazol and clopidogrel.

The anti-inflammatory drug preferably includes, for example, steroids such as dexamethasone, prednisolone and the like.

The bio-derived material includes, for example, EGF (epidermal growth factor), VEGF (vascular endothelial growth factor), HGF (hepatocyte growth factor), PDGF (platelet derived growth factor), BFGF (basic fibroblast growth factor) and the like.

The interferon preferably includes, for example, interferon-γ1a.

The NO production promoting substance preferably includes, for example, L-arginine.

Whether these biologically bioactive substances are used singly as one type of biologically bioactive substance or in combination of two or more different types of biologically bioactive substances should be appropriately determined depending on the case.

The biodegradable polymer is one that is slowly biodegraded in the course of the placement of the intravascular implant of the invention in a lesioned part, and is not critical so far as it does not adversely influence the living body of men or animals. Preferably, the polymer is at least one selected from the group consisting of polyglycollic acid, polylactic acid, polycaprolactone, polyhydroxybutyric acid, cellulose, polyhydroxybutylate valeric acid and a polyorthoester, or a copolymer, mixture or composite material thereof. This is because these are low in reactivity with a living body tissue and is able to inhibit degradation in the blood vessel.

The plasticizer is not critical so far as it does not adversely influence the living body of men or animals and is preferably at least one selected from the group consisting of polyethylene glycol, plyoxyethylenepolyoxypropylene glycol, polyoxyethylene sorbitan monooleate, a monoglyceride and an acetylated monoglyceride, or a mixture thereof. This is because of their low reactivity with a living body tissue and capability of controlling physical properties of a layer containing a biodegradable polymer.

The plasticizer is used in an amount of 0.01 to 80 mass %, preferably 0.1 to 60 mass % and more preferably 1 to 40 mass %, relative to the biodegradable polymer. Such a use ratio is favorable in that miscibility with a biodegradable polymer is good and physical properties of a biodegradable polymer can be appropriately improved.

Although, as stated above, the intravascular implant of the invention preferably has a biologically bioactive substance and a biodegradable polymer in the surface of the implant body of the invention, it is more preferred that the implant body of the invention is formed of a metal material containing gadolinium, neodymium and magnesium alone and is substantially free of components other than those indicated above (i.e. the total of contents of individual components is not larger than 1 mass %) and that the biodegradable polymer used is at least one selected from the group consisting of polylactic acid, polycaprolactone, polyglycollic acid, polyhydroxybutyric acid, cellulose, polyhydroxybutylate valeric acid and a polyorthoester, or a copolymer, mixture or composite material thereof.

The implant body of the invention made of such components as mentioned above and having a biologically bioactive substance and a biodegradable polymer on the surface thereof is gradually decomposed in the blood vessel into hydroxides. If the implant body alone of the invention exists in the blood vessel in the absence of the biodegradable polymer, the vicinity of the implant body of the invention in the blood vessel becomes alkaline. However, polylactic acid or the like used as the biodegradable polymer is gradually decomposed in the blood vessel to release an acid and thus, use of a combination of the implant body of the invention formed of such components as stated hereinabove and the biodegradable polymer such as polylactic acid or the like brings the vicinity of the implant body of the invention close to neutral. In this sense, this is safer to a living body. Moreover, the biologically bioactive substance can also exist stably. The biologically bioactive substance may be changed in quality in an acidic or alkaline environment, for which to keep neutrality is preferred.

The intravascular implant of the invention is of a type which is ordinarily employed for treatment of the blood vessel and is not critical so far as it has the implant body of the invention capable of being manufactured from a metal material of the invention having such a composition as set out hereinbefore.

Examples include a stent, a covered stent, a coil, a microcoil, an artificial blood vessel, an artificial bone, a shield, a wire knit, a clip and a plug.

Further, those having, for example, a lumen supporting function within hollow organs and/or duct systems (urinary duct, bile duct, urethra, uterus, and bronchial tube) may be mentioned.

Alternatively, further mention may be made, for example, of a closing member for use as a closing system for hollow space connection, pulse tube or duct system.

Still alternatively, mention may be made, for example, of a fixing or supporting device for transiently fixing a tissue implant or tissue transplant.

Yet alternatively, mention may be made, for example, of a bolt, a nail, a wire and a plate.

Still yet alternatively, mention may be made, for example, of a stent graft, a vascular stapling device, a vascular hemostatic device, a vascular aneurysm treating device, and an intravascular implant medical device using a stent as a support.

In the intravascular implant of the invention, the implant body of the invention should preferably be tubular in form. This is because of its stable placement in the blood vessel.

The implant body of the invention having such a tubular form includes those bodies which are made of a metal material of the invention and has a substantially cylindrical form with fine openings therein and wherein a wire or fibers made of a metal material of the invention are knit into a cylindrical structure.

Figure 2:
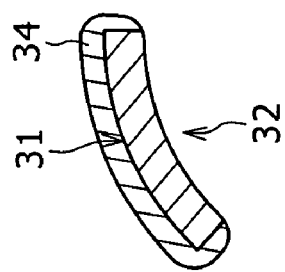
FIG. 2 is an enlarged, cross-sectional view taken along line A-A of FIG. 1.

The intravascular implant of the invention should preferably have an implant body obtained by subjecting the metal material of the invention shaped in a tubular form to laser processing. This is because of the ease in processing of the metal material. As shown in FIG. 2, the section becomes substantially trapezoidal, so that layers made of a biologically bioactive substance and a biodegradable polymer can be stably formed over an upper or lower surface of the trapezoid more easily than with the case of an implant made of a linear member whose section is circular.

The length, size and thickness of the implant body of the invention having a tubular form may vary depending on the purpose in end use and, in general, the length is at 5 to 1000 mm, the size (a diameter substantially in circular section) is at 1 to 50 mm and the thickness is at 0.05 to 0.2 mm.

The intravascular implant of the invention is preferably a stent. This is because it can be readily carried in the blood vessel by means of a balloon catheter and others after reduction in diameter and can be expanded at a narrowed site to keep an adequate lumen. As stated hereinabove, with a stent of the type wherein the content of magnesium in the metal material of the invention is 80 mass % or over, there is achieved an effect that the magnesium ion is liable to be discharged around the stent, so that antithrombogenicity is likely to develop and disappearance in vivo is occurred with the ease.

The stent includes a coil-shaped stent, a net-shaped stent, a tubular stent (a stent made of a tubular body made of a metal or the like with a multitude of through-holes therein), and the like.

The intravascular implant of the invention is preferably a self-expandable stent or a balloon-expandable stent. This is because these stents allow easier delivery thereof into the blood vessel.

The intravascular implant of the invention should preferably be a coronary vascular vessel stent or a peripheral stent.

The peripheral stent used herein means a stent used at the peripheral parts of the blood vessel, e.g. the artery of the brain, the carotid artery, the renal artery, the artery of the lower limb, the thoracic artery, the abdominal artery and the like and preferably has such a shape as shown in FIG. 1 described hereinafter.

For an instance of the intravascular implant of the invention, a stent is illustrated by way of FIG. 1 but should not construed as limiting the intravascular implant of the invention thereto.

In FIG. 1, a stent 1, which is the intravascular implant of the invention, includes a cylindrical body having an opening at opposite terminal ends thereof and extending along the length between the opposite terminal ends. The cylindrical body has a multitude of cut-away portions communicating between the outer and inners sides thereof at a side face of the body, thereby providing a structure wherein when the cut-away portions are deformed, the cylindrical body is radially expandable or contractable and keeps its shape on placement in the blood vessel.

In the embodiment shown in FIG. 1, the stent 1 is formed of a linear member 2 and has a substantially rhombic element 11 having an opening therein as a fundamental unit. A plurality of substantially rhombic elements 11 are continuously disposed and arranged along a direction of the minor axis thereof to provide a cyclic unit 12. The cyclic unit 12 is connected to an adjacent cyclic unit 12 through a linear connection member 13. In this way, a plurality of cyclic units 12 are continuously arranged in an axial direction while combining partly with each other. The stent 1 has such an arrangement as set out above, thereby providing a cylindrical body which is opened at opposite terminal ends thereof and extends along the length thereof between the opposite terminal ends. The stent 1 has a structure having cut-away portions substantially in a rhombic form, wherein when the cut-away portions are deformed, the cylindrical body is expandable or contractable in radial directions.

Where the stent is constituted of the linear member 2, the width of the linear member 2 used to provide the stent 1 as having a multitude of cut-away portions is not critical and is preferably at 0.01 to 0.5 mm and more preferably at 0.05 to 0.2 mm.

The size of the stent 1 may be appropriately selected depending on the portion to be applied. For instance, when applied to a coronary blood vessel, it is preferred that a diameter of a circle in section vertical to the length (a radial direction) prior to expansion (hereinafter referred to simply as "outer diameter") is at 1.0 to 5.0 mm, with a length being at 5 to 50 mm and a thickness being at 0.05 to 0.2 mm.

It will be noted that the stent illustrated above is only by way of an embodiment and the invention widely comprehends structures of cylindrical bodies having an opening at opposite terminal ends thereof and extending between the opposite terminal ends along the length thereof wherein the body has a multitude of cut-away portions communicating between inner and outer sides thereof in the side surface of the body. When the cut-away portions are deformed, the cylindrical body is expandable or contractable in radial directions.

Of these stents, a stent whose linear member 2 has such a sectional form as shown in FIG. 2 (a form wherein an arc of an outer side surface 31 is slightly longer than an arc of an inner side surface 3) is preferred. This is because if the linear member has such a section as mentioned above and the stent body has a content of magnesium of not smaller than 80 mass % relative to the total weight, the magnesium ion concentration around the stent becomes more uniform and higher, thereby enabling clot formation to be more completely inhibited.

Preferably, such a sectional form is used and, as shown in FIG. 2, a layer 34 of a composition including a biologically bioactive substance and a biodegradable polymer (hereinafter referred to as "composition layer 34") is formed on an upper surface (a side opposite to the inner side surface 32) of the outside surface 31. This is for the reason that if the composition layer 34 is formed on the surface of the stent body having such a section, the biologically bioactive substance is released from the stent in a more efficient manner when compared, for example, with the case wherein the section is substantially in circle.

The intravascular implant of the invention can be made by an ordinary method using the metal material of the invention. For an instance, the manufacture of a stent is illustrated.

The respective materials of magnesium and gadolinium (metal pieces, alloy pieces, oxides or the like) are selected in such a way that the composition of a finished stent body is within compositional ranges of the metal material of the invention and melted in an inert gas or in vacuum. If necessary, materials selected from neodymium, zinc, zirconium, calcium and other components are melted together.

Next, the melt is cooled to form an ingot, and the ingot is mechanically polished, followed by hot pressing and extrusion to provide a large-sized pipe. A die drawing step and a thermal treating step are successively repeated to obtain a smaller-sized pipe having a given thickness and outer diameter. An opening pattern is attached on the pipe surface, and portions other than the opening pattern are dissolved out by an etching technique such as laser etching, chemical etching or the like to form openings. Alternatively, according to a laser cutting technique based on pattern information memorized in a computer, the pipe may be cut away in accordance with the pattern to form openings.

Besides, a coil-shaped stent may be made, for example, by a method wherein the ingot is subjected to hot pressing and extrusion to provide a large-sized wire, followed by successively repeating the die drawing step and thermal treating step to obtain a smaller-sized wire having a desired thickness and an outer diameter. The wire is bent to provide a pattern such as a wavy form or the like, and spirally taken up on a mandrel, followed by removal from the mandrel and cutting the patterned wire to a given length.

The stent, which is a kind of intravascular implant according to the invention, can be made by such methods as set out above.

Where an intravascular implant of the invention is of the type that has, on the surface thereof, a layer made of a composition containing such a biologically bioactive substance and biodegradable polymer as set out hereinbefore, or a layer of the biologically bioactive substance and a layer of the biodegradable polymer, it can be made according to the following method.

Such a biologically bioactive substance and biodegradable polymer as discussed before are mixed at such a ratio as indicated before, or are separately dissolved in a solvent such as acetone, ethanol, chloroform, tetrahydrofuran or the like, at a solution concentration of 0.001 to 20 mass %, preferably 0.01 to 10 mass %. According to a conventional procedure using a spray, a dispenser or the like, the solution is applied onto the surface of a stent and the solvent is evaporated.

The intravascular implants of the invention other than the stent, starting materials (materials) are likewise selected and dissolved, followed by molding into an intended shape to provide an implant body of the invention. If necessary, further processing is carried out to make an intravascular implant of the invention.

The method of using the intravascular implant of the invention made according to such methods as set out hereinabove is similar to ordinary ones and is not critical so far as there is used a method that is directly applied to a blood vessel damaged site. For instance, mention is made of a method wherein when a stent is used as an intravascular implant, a balloon catheter is inserted from the groin or the brachial artery for the purpose of expanding the blood vessel of the coronary artery which has become narrowed by arterio sclerosis so as to permit good blood flow, and the balloon is expanded at the narrowed portion to expand the blood vessel (a revascularization procedure using a percutaneous coronary artery intervention technique), after which the balloon is removed and the stent is inserted at the site for expansion.

EXAMPLES

The invention is more particularly described by way of examples. It will be noted that the invention should not be construed as limited to these examples.

Example 1

Substances indicated in Table 1 were used to carry out a cell cytotoxicity test using human vascular smooth muscle cells.

More particularly, human vascular smooth muscle cells were implanted into individual wells of a 96-well microtiter plate along with a culture solution (commercial name: SmGM-2 Bullet kit, made by Cambrex Corporation), followed by cultivation in a carbon dioxide gas incubator at 37° C. for 48 hours. The culture solution dissolving $MgCl_2$ that was used as a chemical substance to be tested was added thereto in every $1 \times 10^{-1}$ M so that a final concentration was at $1 \times 10^{-7}$ to $10^{-1}$ M, followed by cultivation for further 48 hours.

Next, WST-1 (La Roche Ltd.) was added, followed by cultivation for 4 hours. WST-1 taken in the human vascular smooth muscle cells was extracted, and the absorbance at 450 nm of the resulting extract was measured by means of a microreader (commercial name: iEMS reader MF, made by Labsystems Inc.). It will be noted that WST-1 taken in the human vascular smooth muscle cells emits light when oxidized and reduced by means of an electron transmission system of mitochondria. Accordingly, WST-1 emits light by reaction only with living cells.

A graph was made wherein an abscissa indicates a concentration of a chemical substance to be subjected to the cytotoxicity test and an ordinate indicates a ratio of a quantity of emitted light of cells subjected to treatment with a chemical substance to be tested to a quantity of emitted light of non-treated cells for reference. The degree of cell cytotoxicity was quantified as a concentration of a chemical substance ($IC_{50}$ value) at which a ratio of a quantity of a dye taken in the treated cells to a quantity of a dye taken in non-treated cells was at 50%.

Such a test was carried out with respect to other types of chemical substances ($NdCl_2$, $GdCl_2$, $Ycl_3$, $CrCl_2$, and $NiCl_2$) to be subjected to the cytotoxicity test to likewise obtain $IC_{50}$ values. The results are shown in Table 1.

TABLE 1

| Metal salt | IC$_{50}$ (M) |
|---|---|
| MgCl$_2$ | $3.4 \times 10^{-2}$ |
| NdCl$_2$ | $7.4 \times 10^{-2}$ |
| GdCl$_2$ | $8.1 \times 10^{-2}$ |
| Ycl$_3$ | $3.6 \times 10^{-4}$ |
| CrCl$_2$ | $1.1 \times 10^{-4}$ |
| NiCl$_2$ | $7.5 \times 10^{-4}$ |

As will be seen from Table 1, the IC$_{50}$ values of MgCl$_2$, NdCl$_2$ and GdCl$_2$ are about 100 times as high as those of YCl$_3$, CrCl$_2$ and NiCl$_2$ and thus, cell cytotoxicity thereof is very low.

Example 2

In order to evaluate biocompatibility of magnesium alloys, a cell cytotoxicity test of the magnesium alloys indicated in Table 2 below was carried out using human vascular smooth muscle cells.

Using magnesium alloys including ELEKTRON 21 (95.0 mass % magnesium-2.9 mass % neodymium-1.2 mass % gadolinium-0.4 mass % zinc-0.5 mass % zirconium), WE43 (92.2 mass % mangnesium-4.0 mass % yttrium-3.4 mass % neodymium-0.4 mass % zirconium), and WE53 (91.2 mass % mangnesium-5.0 mass % yttrium-3.4 mass % neodymium-0.4 mass % zirconium), the respective magnesium alloys were dissolved in physiological saline and further dissolved in a medium in every of $1 \times 10^{-1}$ mg/ml so that a final concentration was at 10 to 0.001 mg/ml, followed by calculation of IC$_{50}$ values (a concentration at which a half of the cells indicates cytotoxicity) of the respective metals. The results are shown in Table 2.

TABLE 2

Table 2 Human Smooth Muscle Cell Cytotoxicity (IC$_{50}$)

| Alloy | IC$_{50}$ |
|---|---|
| ELEKTRON 21 | 5.20 mg/ml |
| WE 43 | 0.31 mg/ml |
| WE 53 | 0.28 mg/ml |

As a result, it was found that WE43 and WE54, which are both yttrium-containing magnesium alloys, were high in cell cytotoxicity. On the other hand, ELEKTRON 21, which is free of yttrium and contains neodymium and gadolinium of high biocompatibility, was found to be very low in cytotoxicity.

Thus, the results of Examples 1 and 2 revealed that magnesium, neodymium and gadolinium were desirable for use as alloy components for an intravascular implant whose cell cytotoxicity should be low.

Example 3

A stent which is a kind of intravascular implant of the invention was embedded in pig coronary artery to check a change of the embedded site.

A method of making a stent used herein (hereinafter referred to as "stent A") is initially illustrated.

Alloy pieces formed of ELEKTRON 21 were melted in an atmosphere of argon gas.

Next, the melt was cooled to form an ingot, and the ingot was formed into a 5 mm×5 mm×100 mm billet by electric discharging, followed by cutting with a drill to provide a large-sized pipe. This large-sized pipe was subjected to die drawing and thermal treating steps to provide a pipe with an outer diameter of 2.0 mm, a length of 50 mm and a thickness of 100 μm.

An opening pattern was attached to the pipe surface, and portions other than the opening pattern were subjected to laser cutting to form openings in the pipe, thereby obtaining stent A having a configuration as shown in FIG. 1 and having an outer diameter of 2.0 mm and a length of 15 mm.

Figure 3:
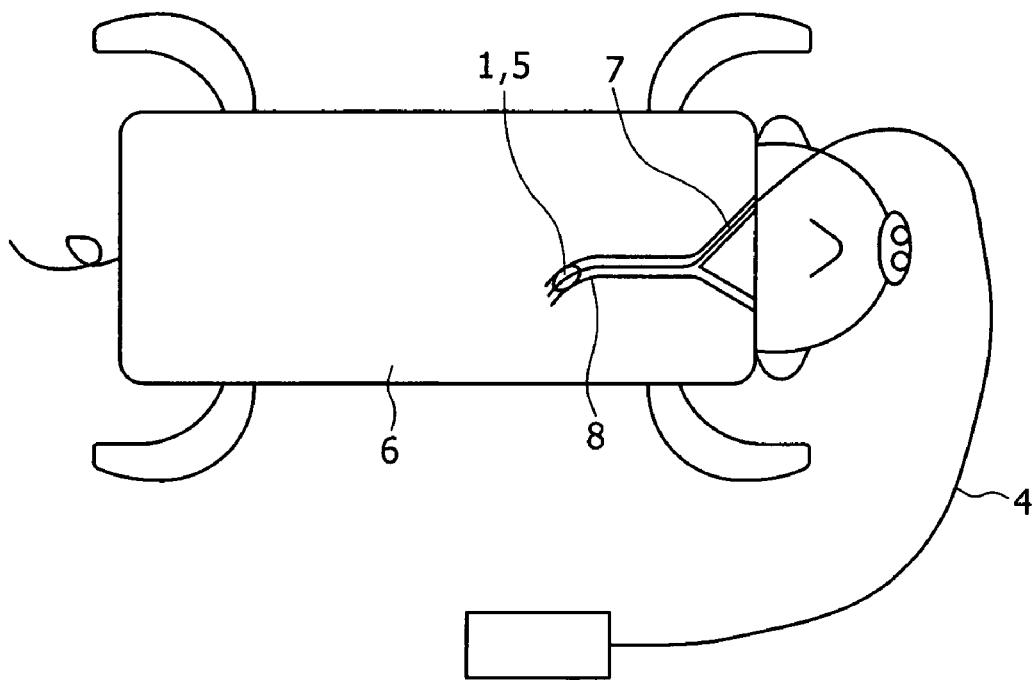
FIG. 3 is an illustrating view showing a site where a stent of Example 3 is embedded in a pig coronary artery.

Stent A made in this way was embedded in pig coronary artery. The embedding method is illustrated with use of FIG. 3.

Initially, part of a pig coronary artery 8 was expanded to an outer diameter of 3.0 mm by use of a balloon catheter. Stent A was subsequently placed on a balloon 5 of a delivery catheter 4 and inserted from a right carotid artery 7 of a pig 6, thereby delivering stent A at part of the pig coronary artery 8 expanded beforehand by use of balloon catheter. The balloon 5 was applied with a pressure of 6 to 18 atm., so that a ratio of an expanded balloon diameter/an imaged blood vessel diameter became 1.1, thereby embedding stent A in the pig coronary artery 8.

Four weeks after the embedding, an autopsy was performed, revealing that stent A was substantially decomposed with a stenosis ratio being at 30%. No intense inflammatory reaction was recognized at the embedded portion of stent A, and a state of inhibiting thickening owing to the proliferation of the smooth muscle cells was observed.

Example 4

A stent of the same type as stent A formed on the surface (outer side surface) thereof with a layer of a composition containing a biologically bioactive substance and a biodegradable polymer as set out hereinbefore to provide a stent (hereinafter referred to as "stent B"). This stent was used to carry out a similar test as in Example 3.

Stent B was made in the following manner.

Initially, sirolimus serving an immunosuppressant was provided as a biologically bioactive substance, polylactic acid (weight average molecular weight of 750,000) provided as a biodegradable polymer, and acetylated monoglyceride provided as a plasticizer. These were used at ratios by weight of biologically bioactive substance:biodegradable polymer:plasticizer=5:4:1 and dissolved in an acetone solvent at a solute concentration of 0.5 mass %.

Next, this solution was sprayed over the surface of a stent similar to stent A by means of a sprayer.

The stent was placed in a vacuum dryer to completely evaporate the acetone solvent.

According to such a method, stent B was made wherein a layer having a weight of about 0.6 mg and an average thickness of 10 μm was formed on the outside surface thereof.

Such stent B was embedded in a pig coronary artery in the same manner as in Example 3 to check a change of the embedded portion.

For weeks after the embedding, stent B was substantially decomposed in 4 weeks, and a stenosis ratio was at 28%. No intense inflammatory reaction was recognized at the embedded portion of stent B, and a state of inhibiting thickening owing to the proliferation of the smooth muscle cells was observed.

Comparative Example 1

A stainless steel stent (material: SUS316L, with an outer diameter of 1.8 mm, a length of 15 mm and a thickness of 80

μm) was used to conduct a test in the same manner as in Example 3. The test conditions were the same as in Example 3 except that the different type of stent was used.

As a result, a stenosis ratio was at 40%. Although no intense inflammatory reaction was recognized at the embedded portion of the stainless steel stent, a thickening state caused by the proliferation of the smooth muscle cells was observed.

Comparative Example 2

For the purpose of comparing a treating effect with a decomposable magnesium alloy stent containing yttrium an embedding test of a magnesium alloy stent (material: WE43, with an outer diameter of 1.8 mm, a length of 15 mm and a thickness of 80 μm) in a pig coronary artery was conducted in the same manner as in Example 3.

Four weeks after the embedding, a stenosis ratio was at 42%.

Four week after the embedding, an autopsy was performed for pathology assessment, revealing that although no intense inflammatory reaction was recognized at the embedded portion of the stent, a thickening state owing to the proliferation of the smooth muscle cells was observed.

From Examples 3, 4 and Comparative Examples 1, 2, it was confirmed that when comparing stents A and B of Examples 3, 4 with the stainless steel stent of Comparative example 1 and the yttrium-containing magnesium alloy stents of Comparative Example 2, a stenosis ratio became lower. Moreover, the comparison between Examples 3 and 4 reveals that a stenosis ratio of Example 4 wherein the biologically bioactive substance is formed on the surface (outside surface) of the stent is lower.

Accordingly, it was confirmed that although stent A of Example 3 which does not have the biologically bioactive substance on the surface (outside surface) adequately shows its function, stent B of Example 4 which has the biologically bioactive substance on the surface (outer surface) thereof is lower in stenosis ratio and is preferred.

The invention claimed is:

1. An intravascular implant comprising an implant body made of a magnesium alloy which contains gadolinium and zirconium elements as a component of said magnesium alloy and is free of yttrium, chromium, nickel, vanadium, silver, mercury, gallium, copper, cobalt and lead elements as a component of said magnesium alloy.

2. The intravascular implant according to claim 1, wherein said magnesium alloy further comprises neodymium.

3. The intravascular implant according to claim 1, wherein a content of said gadolinium ranges 1.0 to 5.0 mass %.

4. The intravascular implant according to claim 2, wherein a content of said neodymium ranges 1.0 to 5.0 mass %.

5. The intravascular implant according to claim 1, wherein said magnesium alloy further comprises zinc.

6. The intravascular implant according to claim 1, wherein said implant body has, on the surface thereof, a layer made of a composition comprising a biologically bioactive substance and a biodegradable polymer.

7. The intravascular implant according to claim 1, wherein said implant body has, on the surface thereof, a layer made of a biologically bioactive substance and a layer made of a biodegradable polymer.

8. The intravascular implant according to claim 6, wherein said biodegradable polymer contains a plasticizer.

9. The intravascular implant according to claim 6, wherein said biologically bioactive substance is at least one member selected from the group consisting of an anticancer drug, an immunosuppressant, an antibiotic, an antirheumatic drug, an antithromobotic drug, an HMG-CoA reductase inhibitor, an ACE inhibitor, a calcium antagonist, an antihyperlipemidic drug, an integrin inhibitor, an antiallergic agent, an antioxidant, a GPIIbIIIa antagonist, a retinoid, a flavonoid, a carotenoid, a lipid improver, a DNA synthesis inhibitor, a tyrosine kinase inhibitor, an antiplatelet drug, an anti-inflammatory drug, a bio-derived material, an interferon and an NO production promoter.

10. The intravascular implant according to claim 6, wherein said biodegradable polymer is at least one member selected from the group consisting of polyglycollic acid, polylactic acid, polycaprolactone, polyhydroxybutyric acid, cellulose, polyhydroxybutylate valeric acid and a polyorthoester, or a copolymer, mixture or composite material thereof.

11. The intravascular implant according to claim 8, wherein said plasticizer is at least one member selected from the group consisting of polyethylene glycol, polyoxyethylenepolyoxypropylene glycol, polyoxyethylenesorbitan monooleate, a monoglyceride and an acetylated monoglyceride, or a mixture thereof.

12. The intravascular implant according to claim 1, wherein said implant body is one obtained by laser processing of said magnesium alloy having a tubular form.

13. The intravascular implant according to claim 1, wherein the implant is a stent.

14. The intravascular implant according to claim 13, wherein said stent is a self-expandable stent or a balloon-expandable stent.

15. The intravascular implant according to claim 13, wherein said stent is a coronary vascular stent or a peripheral stent.

16. An intravascular implant comprising an implant body made of a magnesium alloy that is free of yttrium, chromium, nickel, vanadium, silver, mercury, gallium, copper, cobalt and lead elements as a component of said magnesium alloy, the magnesium alloy including magnesium in an amount not less than 80 mass %, the magnesium alloy also including gadolinium and zirconium elements as a component of said magnesium alloy.

17. The intravascular implant according to claim 16, wherein the magnesium alloy further includes neodymium.

18. The intravascular implant according to claim 17, wherein a content of the gadolinium in the magnesium alloy is 1.0 to 5.0 mass %.

19. The intravascular implant according to claim 16, wherein a content of the gadolinium in the magnesium alloy is 1.0 to 5.0 mass %.

* * * * *